US006534099B1

(12) United States Patent
Bessette et al.

(10) Patent No.: US 6,534,099 B1
(45) Date of Patent: Mar. 18, 2003

(54) PESTICIDAL COMPOSITIONS CONTAINING MENTHYL SALICYLATE

(75) Inventors: Steven M. Bessette, Brentwood, TN (US); Essam E. Enan, Franklin, TN (US)

(73) Assignee: Ecosmart Technologies, Inc., Franklin, TN (US)

( * ) Notice: Subject to any disclaimer, the term of this patent is extended or adjusted under 35 U.S.C. 154(b) by 0 days.

(21) Appl. No.: 09/578,707

(22) Filed: May 26, 2000

Related U.S. Application Data

(63) Continuation-in-part of application No. 08/657,585, filed on Jun. 7, 1996, now Pat. No. 6,114,384, which is a continuation-in-part of application No. 08/553,475, filed as application No. PCT/US94/05823 on May 20, 1994, now Pat. No. 5,693,344, which is a continuation-in-part of application No. 08/065,594, filed on May 21, 1993, now Pat. No. 5,439,690.

(51) Int. Cl.[7] .................. A01N 37/40; A01N 37/10; A01N 37/02; A01N 31/16; A01N 65/00
(52) U.S. Cl. .................. 424/757; 514/544; 514/546; 514/547; 514/733; 514/919; 424/DIG. 10
(58) Field of Search .................. 514/544, 546, 514/919, 733, 547; 424/757, DIG. 10

(56) References Cited

U.S. PATENT DOCUMENTS 3,288,840 A    11/1966    Pawloski .................. 560/71

FOREIGN PATENT DOCUMENTS

| FR | 2 755 825 | A | 5/1988 |
| GB | 704 879 | A | 3/1954 |
| WO | 97/29638 | A | 8/1997 |
| WO | 00/05964 | * | 2/2000 |
| WO | 01/00032 | A1 | 1/2001 |
| WO | 01/00033 | A1 | 1/2001 |

OTHER PUBLICATIONS

King, W.V. Chemicals evaluated as insecticides and repellents at Orlando, FLA. U.S. Department of Agriculture, Agriculture Handbook No. 69, 1954, pp. 6–7 and 306–307.*

* cited by examiner

Primary Examiner—John Pak
(74) Attorney, Agent, or Firm—McDermott, Will & Emery

(57) ABSTRACT

Pesticidal compositions against pests comprising menthyl salicylate. Pesticidal compositions for the control of household insects containing menthyl salicylate with one or more plant essential oils. In addition, the present invention is directed to a method for controlling ants, cockroaches and other household insects by applying an pesticidally-effective amount of the above pesticidal compositions to a locus where pest control is desired.

4 Claims, No Drawings

PESTICIDAL COMPOSITIONS CONTAINING MENTHYL SALICYLATE

CROSS REFERENCE TO RELATED APPLICATIONS

This application is a continuation-in-part of allowed U.S. application Ser. No. 08/657,585, filed Jun. 7, 1996, which is, in turn, a continuation-in-part of application Ser. No. PCT/US94/05823, filed May 20, 1994, now in the U.S. national phase Ser. No. 08/553,475, filed Nov. 9, 1995, which is, in turn, a continuation-in-part of U.S. patent application Ser. No. 08/065,594 filed May 21, 1993 which is now U.S. Pat. No. 5,439,690, issued Aug. 8, 1995. The entire disclosures of the above-identified patent applications are incorporated herein by reference and the benefit of each is hereby claimed.

FIELD OF THE INVENTION

The present invention relates, in general, to pesticidal compositions comprising menthyl salicylate. The present invention also relates to synergistic compositions comprising menthyl salicylate in combination with metabolic detoxication inhibitors, piperonyl butoxide (PBO) and signal transduction modulators, such as tyrosine kinase family member inhibitors, (e.g. genistein). The present invention further relates to synergistic composition comprising menthyl salicylate in combination with a unique delivery system (e.g. solvents). This delivery system helps menthyl salicylate to penetrate the target organism and to subsequently be transported to the site of action at a concentration sufficient to kill the insects. The present invention relates, also, to pesticidal compositions containing menthyl salicylate with one or more plant essential oils and/or derivatives thereof to be used as a contact insecticide and repellent against household insects.

BACKGROUND OF THE INVENTION

Pests (invertebrates, insects, arachnids, larvae thereof, etc.) are annoying to humans for a myriad of reasons. Over the years, synthetic chemical pesticides have provided an effective means of pest control. For example, one approach teaches the use of complex, organic insecticides, such as disclosed in U.S. Pat. Nos. 4,376,784 and 4,308,279. Other approaches employ absorbent organic polymers for widespread dehydration of the insects. See, U.S. Pat. Nos. 4,985,251; 4,983,390; 4,818,534; and 4,983,389. Use of inorganic salts as components of pesticides has also been tried, as disclosed in U.S. Pat. Nos. 2,423,284 and 4,948,013, European Patent Application No. 462 347, Chemical Abstracts 119(5):43357q (1993) and Farm Chemicals Handbook, page c102 (1987).

However, it has become increasingly apparent that the widespread use of synthetic chemical pesticides has caused detrimental environmental effects that are harmful to humans and other animals. For instance, the public has become concerned about the amount of residual chemicals that persist in food, ground water and the environment, and that are toxic, carcinogenic or otherwise incompatible to humans, domestic animals and/or fish. Moreover, some target pests have even shown an ability to develop resistance to many commonly used synthetic pesticides. In recent times, regulatory guidelines have encouraged a search for potentially less dangerous pesticidal compositions via stringent restrictions on the use of certain synthetic pesticides. As a result, elimination of effective pesticides from the market has limited economical and effective options for controlling pests. As an alternative, botanical pesticides are of great interest because they are natural pesticides, i.e.; toxicants derived from plants that are safe to humans and the environment.

The problem is even more evident with respect to the treatment of household insects such as cockroaches and ants. Furthermore, the potential toxicity of pesticides is of great concern in the control of human body louse, where the treatment of children and other humans demand certain safety attributes.

Accordingly, there is a great need for novel and effective pesticidal compositions, containing no synthetic pyrethroids, chlorinated hydrocarbons, organophosphates, carbamates and the like, to be used against human body louse and house hold insects. This patent, however, described only the invention of a novel chemical(s) that is highly effective against American and German cockroaches; black ants and harvester ants.

SUMMARY OF THE INVENTION

A primary object of the present invention is to provide a safe and novel pesticidal composition for use against household insects.

Another object of the invention is to provide novel pesticidal compositions containing menthyl salicylate with and without one or more plant essential oils and/or derivatives thereof, natural or synthetic, as a contact insecticide for the control of house hold insects.

It is also an object of the present invention to provide a delivery system that will increase the efficacy of the novel insecticide for controlling household insects.

It is still another object to provide an pesticidal composition and method that has a pleasant scent or is unscented, and that can be applied without burdensome safety precautions.

It is still another object to provide an pesticidal composition and method as described above which can be inexpensively produced or employed.

It is yet another object of the invention to provide an pesticidal composition and method to which insects cannot build resistance.

It is yet another object of the present invention to provide a safe pesticidal composition that can be applied before detection of house hold insects, as a repellent, such as dust or granules.

It is another object of the present invention to provide a synergistic system that will reduce the required concentration of active ingredients, which will increase the safety, and efficacy of the invented insecticide and/or pesticidal blend.

It is another object of the present invention to apply the signal transduction concept to increase the safety and efficacy of menthyl salicylate and other invented blends.

The above and other objects are accomplished by the present invention which is directed to a contact and/or repellent pesticidal composition against household pests, e.g., ants and cockroaches, comprising in admixture with an acceptable carrier, menthyl salicylate. The present invention is also directed to pesticidal compositions comprising menthyl salicylate and at least one plant essential oil and/or a derivative thereof, natural or synthetic, in admixture with suitable carriers. In addition, the present invention is directed to a method for controlling household insects by applying a pesticidally-effective amount of the above pesticidal compositions to a location where pest control is desired.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety.

Menthyl salicylate ($C_{17}H_{24}O_3$) is a 2-hydroxybenzoic acid 5-methyl-2-(1-methylethyl)cyclohexyl ester. In one embodiment, the present invention provides an pesticidal composition comprising, in admixture with a suitable carrier and optionally with a suitable surface active agent, comprising menthyl salicylate with one or more plant essential oil compounds and derivatives thereof, natural or synthetic, including racemic mixtures, enantiomers, diastereomers, hydrates, salts, solvates and metabolites, etc.

The plant essential oil or derivative thereof, may be comprised of a monocyclic, carbocyclic ring structure having six-members and is substituted by at least one oxygenated or hydroxyl functional moiety. Examples of plant essential oils encompassed within the present invention, include, but are not limited to, members selected from the group consisting of aldehyde C16 (pure), eugenol, phenylethyl propionate, benzyl alcohol, citronellal, and cinnamic alcohol. The plant essential oils may also include known compounds such as pyrethrins, neem oil, and sesame oil. As these plant essential oil compounds are known and used for other uses, they may be prepared by a skilled artisan by employing known methods. In addition, the tyrosine kinase family member inhibitors, for example genistein, will be used as a pure chemical or through other sources that contain genistein such as soybean oil, are included in this invention.

In a preferred embodiment, the present invention is directed to an pesticidal composition for controlling household insects comprising a mixture of one or more of plant essential oil family members with menthyl salicylate. These members include, but are not limited to, eugenol, phenylethyl propionate, benzyl alcohol, cinnamic alcohol or citronellal. These mixtures will be mixed with or without a synergist such as pyrethrins, sesame oil or piperonyl butoxide with a suitable solvent carrier such as Isopar M and/or soybean oil or other vegetable oils. Data below shows that this embodiment is highly effective, i.e. exhibited contact mortality and repellency against American cockroaches, German cockroaches, black ants and red ants (harvester).

It will be appreciated by the skilled artisan that the pesticidal compositions of the present invention unexpectedly exhibit excellent pesticidal activities using one or more U.S. F.D.A. approved plant essential oils, in lieu of conventional synthetic pesticides which are not safe for use around humans and other sensitive areas. Without wishing to be bound by the following theories, it is believed that menthyl salicylate acts at- or closer to- octopaminergic system in insects. Alternatively, menthyl salicylate might attack certain components of signal transduction cascade. Plant essential oils might antagonize a pest's nerve receptors or may act as Phase I and/or Phase II drug metabolizing enzyme inhibitors. Alternatively, plant essential oils may act via an alternative mode of action. The plant essential oils may act as agonists or antagonists against the octopamine receptors that are distinct to invertebrates. In any event, the net effect of the toxicity and action of the inventive composition disclosed herein is heretofore unknown and unexpected.

Use of pesticidal compositions of the present invention generally results in 100% mortality on contact, along with good repellency and residual control. As such, they are advantageously employed as pesticidal agents in uses such as, without limitation, emulsifiable concentrates, wettable powders, dust, and granules for control of household insects. They may also be used in combination with other pesticidally active compounds, to increase their efficacy and/or reduce their toxicity against non-target species, generally making conventional pesticides more acceptable.

The term "carrier" as used herein means an inert or fluid material, which may be inorganic or organic and of synthetic or natural origin, with which the active compound is mixed or formulated to facilitate its application to the location to be treated, or its storage, transport and/or handling. In general, any of the materials customarily employed in formulating pesticides, herbicides, or fungicides, are suitable. The inventive pesticidal compositions of the present invention may be employed alone or in the form of mixtures with such solid and/or liquid dispersible carrier vehicles and/or other known compatible active agents such as other pesticides, or pediculicides, acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The pesticidal compositions of the present invention can be formulated or mixed with, if desired, conventional inert pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, and formulations used with burning equipment, such as fumigating cartridges, fumigating cans and fumigating coils, as well as ULV cold mist and warm mist formulations, etc.

Formulations containing the pesticidal compositions of the present invention may be prepared in any known manner, for instance by extending the pesticidal compositions with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the pesticidal compositions of the present invention. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

Liquid concentrates may be prepared by dissolving a composition of the present invention with a solvent and dispersing the pesticidal compositions of the present inventions in water with the acid of suitable surface active emulsifying and dispersing agents. Examples of conventional carrier vehicles for this purpose include, but are not limited to, aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.). paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g. kaolins, clays, vermiculite, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.).

Surface-active agents, i.e., conventional carrier vehicle assistants, that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which acts carriers for the pesticide. These finely divided solids preferably have an average particle size of less than about 50 microns. A typical dust formulation useful for controlling pests contains 1 part of pesticidal composition and 99 parts of diatomaceous earth or vermiculite. Granules may comprise porous or nonporous particles. The granule particles are relatively large, a diameter of about 400–2500 microns typically. The particles are either impregnated or coated with the inventive pesticidal compositions from solution. Granules generally contain 0.05–15%, preferably 0.5–5%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

In commercial applications, the present invention encompasses carrier composition mixtures in which the pesticidal compositions are present in an amount substantially between about 0.01–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

Furthermore, the present invention encompasses methods for killing, combating or controlling pests, which comprises applying to at least one of correspondingly (a) such pests and (b) the corresponding habitat thereof, i.e. the locus to be protected, e.g. to the household, a correspondingly combative, an pesticidally effective amount, or toxic amount of the particular pesticidal compositions of the invention alone or together with a carrier as noted above. The instant formulations or compositions may be applied in any suitable usual manner, for instance by spraying, atomizing, vaporizing, dusting, watering, squirting, sprinkling, pouring, fumigating, and the like. The method for controlling household insects comprises applying the inventive composition, ordinarily in a formulation of one of the aforementioned types, to a locus or area to be protected from the house hold insects. The compound, of course, is applied in an amount sufficient to effect the desired action. This dosage is dependent upon many factors, including the targeted pest, the carrier employed, the method and conditions of the application. Proper consideration and resolution of these factors to provide the necessary dosage of the active compound at the site to be protected are within the skill of those versed in the art. In general, however, the effective dosage of the compound of this invention at the locus to be protected-i.e., the dosage with which the pest comes in contact-is of the order of 0.001 to 5.0% based on the total weight of the formulation, though under some circumstances the effective concentration will be as little as 0.0001% or as much as 20%, on the same basis.

The pesticidal compositions and methods of the present invention are effective against different species of household insects, including American cockroaches, German cockroaches, black ants and red ants (harvester), and it will be understood that these insects exemplified and evaluated in the working Examples herein is representative of such a wider variety.

The composition and method of the present invention will be further illustrated in the following, non-limiting Examples. The Examples are illustrative of various embodiments only and do not limit the claimed invention regarding the materials, conditions, weight ratios, process parameters and the like recited herein.

EXAMPLE

Test Materials
  Menthyl salicylate: $C_{17}H_{24}O_3$.
  Plant essential oils: phenylethyl propionate, eugenol, benzyl alcohol, cinnamic alcohol and citronellal
  Synergists: piperonyl butoxide (PBO), sesame oil, and pyrethrins.
  Carrier: methylated soybean oil and Isopar M. Soybean oil is also used as a source of genistein, the inhibitor for signal transduction protein tyrosine kinase family members.
  Test insects: American cockroaches, German cockroaches, black ants and red ants (harvester).

Experimental Design

Study A

To Determine Whether Menthyl Salicylate Acts as Killing Agent Against Household Insects
Experiment 1: To determine the lethal activity of menthyl salicylate against cockroaches. Menthyl salicylate was tested at 250 mg/jar against German cockroaches. Two replicates were used in this study. Three adult German cockroaches were used per replicate. Continuous exposure was performed with "walk-across". All controls and treated roaches were under continuous observations for 6 hrs.
Results: 30% KD (knock-down) was found 20 min after exposure. 100% mortality (M) was found 24 hr after continuous exposure.
Conclusion: Menthyl salicylate is good killing agent at this rate of application.

Study B

To determine whether menthyl salicylate can synergize the efficacy of eugenol and/or PEP against German cockroaches.
Experiment 1. To determine whether menthyl salicylate acts as a synergist to eugenol and /or PEP blend. This experiment was also conducted against German cockroaches as described in Study A. Several blends of Eugenol/PEP were tested. These blends are:

|  | Concentration, mg/jar | | | | |
| --- | --- | --- | --- | --- | --- |
|  | ES6 | ES12 | ES13 | ES6a | ES12a |
| Eugenol | 50 | 50 | 0 | 50 | 50 |
| PEP | 200 | 200 | 0 | 125 | 125 |
| Menthyl salicylate | 0 | 250 | 250 | 0 | 4 |

Results
This experiment was repeated twice and the data was consistent.
KD = knock-down   M = mortality.

| Test blend | number of insects | KD/M | time |
| --- | --- | --- | --- |
| ES6 | 3 | 1/0 | 2 min |
|  |  | 1/1 | 3 min |
|  |  | 1/0 | 4 min |
|  |  | 1/1 | 3 hr |
|  |  | 0/1 | 24 hr |
| ES12 | 3 | 1/1 | 5 sec |
|  |  | 1/0 | 1 min |
|  |  | 1/1 | 1½ min |
|  |  | 1/1 | 4 min |
| ES13 | 3 | 1/0 | 20 min |
|  |  | 1/3 | 24 hr |
| ES6a | 3 | 1/0 | 6 min |
|  |  | 1/0 | 9 min |
|  |  | 1/1 | 70 min |
|  |  | 1/2 | 3 hr |
| ES12a | 3 | 0/1 | 15 min |
|  |  | 0/1 | 60 min |
|  |  | 0/1 | 90 min |

Conclusion: Menthyl salicylate at 4–250 mg synergizes the efficacy of eugenol/PEP against German cockroaches. The efficacy of the test blends was dose- and time-dependent.

Study C-1

Menthyl salicylate was tested in the presence and absence of PBO against American cockroaches, German cockroaches, red ants (harvesters) and black ants to address the following:
1—Species differences/specificity
2—Synergy-relationship between menthyl salicylate and PBO
3—Impact of Isopar M (delivery system) on the efficacy of these blends
4—Impact of soybean oil as solvent and as a source for genistein, the tyrosine kinase family member inhibitor on the efficacy of test chemicals
5—Therefore, different blends that are menthyl salicylate/PBO-base were prepared for testing:

|  | Concentration, mg/jar | | | | |
| --- | --- | --- | --- | --- | --- |
| Test Blend | ENa | ENb | ENc | ENe | ENf |
| Menthyl salicylate | 100 | 100 | 100 | 100 | 100 |
| PBO | 200 | 200 | 200 | 200 | 0 |
| Isopar M | 0 | 250 | 0 | 200 | 200 |
| Soybean oil | 0 | 0 | 250 | 200 | 200 |

Three roaches were used per test blend
Same jars that were used for American cockroaches were used later for German cockroaches Results

|  | American cockroach | | German cockroach | |
| --- | --- | --- | --- | --- |
| Test blend | KD/M | Time | KD/M | Time |
| ENa | 1/0 | 90 min | 1/0 | 2 min |
|  | 1/0 | 6 hr | 2/0 | 4 min |
|  |  |  | 3/3 | 10 min |
| ENb | 0/1 | 12 min | 0/1 | 1 min |
|  | 2/0 | 20 min | 1/0 | 2 min |
|  | 2/2 | 120 min | 2/1 | 4 min |
|  |  |  | 1/1 | 5 min |
| ENc | 1/0 | 27 min | 1/0 | 1 min |
|  | 1/1 | 28 min | 3/1 | 2 min |
|  | 1/0 | 40 min | 2/2 | 2½ min |
|  | 1/2 | 43 min |  |  |
| ENe | 0/1 | 5 min | 0/1 | 1 min |
|  | 0/2 | 7 min | 1/0 | 90 sec |
|  |  |  | 1/1 | 100 sec |

-continued

| | | | 1/1 | 3 min |
|---|---|---|---|---|
| ENf | 0/1 | 30 min | 1/0 | 1 min |
| | 0/0 | 6 hr | 1/2 | 2 min |
| | | | 0/1 | 8 min |

Conclusion

1—Comparing blend ENb vs ENc, it is clear that the blend with Soybean oil (source for genistein, the tyrosine kinase inhibitor) acts faster than the blend with Isopar M 2—Replacing Isopar M with Soybean oil increased the efficacy of menthyl salicylate/PBO mixture against German cockroaches and American cockroaches (blend ENb vs blend ENc) as judged by the $LT_{100}$ values (time elapsed between exposure and 100% mortality among the exposed insects).

3—Slight increase in the efficacy of menthyl salicylate/ PBO (blend ENe) against German cockroaches was found when they were mixed together with Soybean oil and Isopar M. However, a substantial increase in the efficacy of menthyl salicylate/PBO was demonstrated against American cockroaches in the presence of both soybean oil and Isopar M.

4—As judged by the $LT_{100}$, mixing menthyl salicylate/ PBO with soybean oil was more potent against roaches than Isopar M as summarized below $LT_{100}$=Time elapsed between exposure and 100% mortalilty of exposed insects.

| | $LT_{100}$ | |
|---|---|---|
| | German cockroaches | American cockroaches |
| Menthyl salicylate + PBO (only) | 10 min | 6 hrs |
| W/Isopar M | 5 min | 120 min |
| W/soybean oil | 2½ min | 43 min |
| W/Isopar M and soybean oil | 3 min | 7 min |

In the absence of PBO, the $LT_{100}$ against German cockroaches and American cockroaches were increased as follows:

| | $LT_{100}$ | |
|---|---|---|
| blend ENe vs blend ENf | W/PBO | W/O PBO |
| German cockroaches | 3 min | 8 min |
| American cockroaches | 7 min | 6 hr |

Study C-2

Five ants were used per test blend

Same treated jars that were previously used (see Study C-1) for roaches testing were used 48 hr later against ants (i.e. 48 hr residual toxicity).

| | Results | | | |
|---|---|---|---|---|
| | black ants | | harvester | |
| Test blend | KD/M | Time | KD/M | Time |
| ENa | ND | | ND | |
| ENb | 1/0 | 3 min | 0/1 | 25 min |
| | 1/1 | 15 min | 0/1 | 35 min |
| | 4/4 | 55 min | 0/3 | 55 min |
| ENc | 2/0 | 12 min | 0/1 | 9 min |
| | 1/0 | 20 min | 0/3 | 12 min |
| | 5/2 | 120 min | 0/1 | 20 min |
| | 3/3 | 16 min | | |
| ENe | 0/1 | 30 sec | 0/1 | 2 min |
| | 0/1 | 2 min | 0/1 | 7 min |
| | 3/3 | 5 min | 0/1 | 15 min |
| | | | 0/1 | 16 min |
| | | | 0/1 | 17 min |
| ENf | 2/0 | 30 min | 0/2 | 1 min |
| | 1/0 | 6 hr | 0/1 | 2 min |
| | 5/5 | 60 min | 0/1 | 8 min |
| | | | 0/2 | 90 min |

Conclusion $LT_{100}$ (48 hr residual activity)

| | Menthyl salicylate/ PBO | W/Isopar M | W/ soybean oil | W/both |
|---|---|---|---|---|
| Black ants | 100 min | 55 min | 16 min | 5 min |
| Red ants | 90 min | 55 min | 20 min | 17 min |

Note:
In all assays menthyl salicylate was used at 100 mg/jar and PBO was used at 200 mg/jar.
The test was run in the presence of 200 mg/jar of soybean oil and 200 mg/jar of isopar M.
It should be mentioned that roaches were exposed to the treated jars 1 hr after jars treatment. While, ants were exposed to the same jars 48 hr after jars treatment and roaches testing.

| | $LT_{100}$ | |
|---|---|---|
| | W/PBO | W/O PBO |
| Black ants | 5 min | 60 min |
| Red ants | 17 min | 90 min |

Study D

Further studies were performed to address the synergy/ antagonistic properties between menthyl salicylate and other plant essential oils.

In particular the synergistic/antagonistic action of menthyl salicylate against the efficacy of each of PEP, eugenol, citronellal and cinnamic alcohol were tested against harvester ants as testing model.

For the synergy-relationship between PBO and menthyl salicylate, the following blends were tested

| | Concentration, mg/jar | | |
|---|---|---|---|
| Test blend | ENg | ENh | ENi |
| Menthyl salicylate | 100 | 100 | 100 |
| Soybean oil | 200 | 200 | 200 |
| PBO | 0 | 100 | 50 |

For whether PBO or isopar M are essential factors for the efficacy of menthyl alcohol against ants the following blends were tested:

|  | Concentration mg/jar | | | | | |
|---|---|---|---|---|---|---|
| Test blend | ENd | ENg | ENj | ENk | ENl | ENm |
| Menthyl salicylate | 100 | 100 | 100 | 100 | 100 | 100 |
| Soybean oil | 200 | 200 | 200 | 200 | 200 | 200 |
| PBO | 200 | 0 | 0 | 0 | 50 | 50 |
| PEP | 62.5 | 0 | 0 | 0 | 0 | 0 |
| Isopar M | 200 | 0 | 0 | 0 | 0 | 0 |
| Citronellal | 0 | 0 | 25 | 0 | 0 | 25 |
| Cinnamic alcohol | 0 | 0 | 0 | 25 | 25 | 0 |

| | Results | | |
|---|---|---|---|
| Test Blend | number of ants | KD/M | Time |
| ENd | 5 | 0/1 | 10 min |
| | | 0/1 | 18 min |
| | | 0/1 | 21 min |
| | | 0/3 | 25 min |
| ENg | 5 | 0/2 | 4 min |
| | | 0/1 | 5 min |
| | | 0/1 | 6 min |
| | | 0/1 | 11 min |
| ENh | 5 | 0/1 | 4 min |
| | | 0/1 | 9 min |
| | | 0/1 | 10 min |
| | | 0/1 | 12 min |
| | | 0/1 | 21 min |
| ENi | 5 | 0/1 | 2 min |
| | | 0/2 | 8 min |
| | | 0/1 | 10 min |
| | | 0/1 | 13 min |
| ENj | 5 | 0/1 | 3 min |
| | | 0/2 | 9 min |
| | | 0/1 | 17 min |
| | | 0/1 | 30 min |
| ENk | 5 | 0/1 | 5 min |
| | | 0/1 | 11 min |
| | | 0/1 | 16 min |
| | | 0/1 | 22 min |
| | | 0/1 | 26 min |
| ENl | 5 | 0/1 | 5 min |
| | | 0/1 | 7 min |
| | | 0/1 | 13 min |
| | | 0/1 | 15 min |
| ENm | 5 | 0/2 | 2 min |
| | | 0/1 | 6 min |
| | | 0/2 | 8½ min |

Conclusion $LT_{100}$ values for menthyl salicylate blend, tested against harvester ants, as calculated from data of study D.

| | $LT_{100}$ | |
|---|---|---|
| | W/PBO | W/O PBO |
| PEP | 25 min | ND |
| Cinnamic alcohol | 15 min | 26 min |
| Citronellal | 8½ min | 30 min |

Note: In all assays menthyl salicylate was used at 100 mg/jar and soybean oil was used at 200 mg/jar. No Isopar M was used except with PEP

| | $LT_{100}$ | | | |
|---|---|---|---|---|
| | W/PBO concentrations, mg/jar | | | |
| | 0 | 50 | 100 | 200 |
| Menthyl salicylate/ Soybean oil | 11 min | 13 min | 21 min | ND |

Note: In all assays menthyl salicylate was used at 100 mg/jar and soybean oil was used at 200 mg/jar. No Isopar M was used.

| | $LT_{100}$ | |
|---|---|---|
| Test Blend | W/PEP | W/O PEP |
| Menthyl salicylate/PBO/ Soybean oil/Isopar M | 5 min (fresh prep.) | 17 min (48 hr residual) |

Note: PEP was used at 62.5 mg/jar. In all assays menthyl salicylate was used at 100 mg/jar, PBO was used at 200 mg/jar, soybean oil and Isopar M each were used at 200 mg/jar.

Study E

Objectives of this Study are

To address whether the efficacy of PEP will be increased with menthyl salicylate/soybean oil against harvester and black ants.

To address whether Isopar M is required for the efficacy of PEP/menthyl salicylate/soybean oil To address whether menthyl salicylate/soybean oil will provide a safe and good killing agent Materials glass petri dishes 100 mm were used in this study all treated dishes kept open during the time of exposure

| | Concentration, mg/jar | | | | | | |
|---|---|---|---|---|---|---|---|
| Test blend | ENn | ENo | ENp | ENq | ENr | ENs | ENt |
| Menthyl salicylate | 100 | 100 | 100 | 100 | 100 | 100 | 100 |
| Soybean oil | 200 | 200 | 200 | 200 | 200 | 200 | 0 |
| Isopar M | 200 | 200 | 0 | 0 | 0 | 0 | 0 |
| PBO | 200 | 200 | 200 | 200 | 0 | 0 | 200 |
| PEP | 0 | 62.5 | 0 | 62.5 | 62.5 | 0 | 0 |

- Five ants were used per test blend

| | Results | | | |
|---|---|---|---|---|
| | harvester | | black ants | |
| Test blend | M | Time | M | Time |
| ENn | 2 | 30 sec | 1 | 1 min |
| | 2 | 60 sec | 2 | 10 min |
| | 1 | 90 sec | 2 | 15 min |
| ENo | 3 | 2 min | 1 | 1 min |
| | 1 | 3 min | 1 | 2 min |
| | 1 | 5 min | 3 | 16 min |
| ENp | 1 | 2 min | 2 | 18 min |
| | 1 | 3 min | 1 | 20 min |
| | 3 | 6 min | 2 | 26 min |
| ENq | 2 | 1 min | 2 | 10 min |
| | 1 | 1½ min | 1 | 11 min |
| | 2 | 3 min | 2 | 12 min |
| ENr | 2 | 2 min | 1 | 20 min |
| | 1 | 4 min | 1 | 22 min |
| | 1 | 4½ min | 2 | 35 min |
| | 1 | 10 min | 1 | 37 min |
| ENs | 2 | 3 min | 1 | 18 min |
| | 2 | 5 min | 2 | 25 min |
| | 1 | 11 min | 2 | 40 min |
| ENt | 3 | 11 min | 1 | 25 min |
| | 1 | 18 min | 1 | 40 min |
| | 1 | 35 min | 3 | 65 min |

M = mortality

Conclusion

1—in the presence of Isopar M, antagonistic effect was found when PEP was mixed with menthyl salicylate and soybean oil (blend ENo vs ENq).

2—in the absence of Isopar M, a synergistic effect of PEP efficacy was found when it was mixed with menthyl salicylate/PBO/soybean oil. The LT100 was reduced by 50% (blend ENp vs ENq).

3—In the absence of PBO, a 100% mortality within 10 min following harvester exposure was found when PEP was mixed with menthyl salicylate and soybean oil (ENq vs ENr).

4—Menthyl salicylate gave 100% M within 11 and 40 min against harvester and black ants, respectively, when it was mixed with soybean oil From the Above Data, it can be Concluded that 1—Isopar M is not required when soybean oil is used 2—PBO is a good synergist for PEP/menthyl salicylate/soybean oil. However, high efficacy can be obtained with the same mixture without PBO 3—Menthyl salicylate/soybean oil is a good killing agent without any other chemicals.

As can be seen from the above discussion, the pesticidal combinations of active compounds according to the present invention are markedly superior to known pesticidal agents/active compounds conventionally used for control of household insects.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A pesticidal composition for the control of household insects, comprising, in admixture with an acceptable carrier, menthyl salicylate, phenylethyl propionate, and eugenol.

2. A method for controlling household insects, which comprises applying to a locus where control is desired a pesticidaldy-effective amount of the composition of claim 1.

3. A pesticidal composition for the control of household insects, comprising, in admixture with an acceptable carrier, menthyl salicylate, phenylethyl propionate and soybean oil.

4. A method for controlling household insects, which comprises applying to a locus where control is desired a pesticidally-effective amount of the composition of claim 3.

* * * * *